United States Patent
Fiss

(10) Patent No.: US 11,920,185 B2
(45) Date of Patent: Mar. 5, 2024

(54) METHOD OF INACTIVATING MICROBES BY CITRACONIC ANHYDRIDE

(71) Applicant: Roche Molecular Systems, Inc., Pleasanton, CA (US)

(72) Inventor: Ellen Fiss, Albany, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 349 days.

(21) Appl. No.: 17/233,744

(22) Filed: Apr. 19, 2021

(65) Prior Publication Data
US 2021/0238654 A1    Aug. 5, 2021

Related U.S. Application Data

(62) Division of application No. 15/569,361, filed as application No. PCT/EP2016/061705 on May 24, 2016, now Pat. No. 11,015,217.

(60) Provisional application No. 62/168,541, filed on May 29, 2015.

(51) Int. Cl.
*C12Q 1/6806* (2018.01)
*C07D 307/60* (2006.01)
*C12Q 1/6809* (2018.01)
*C12Q 1/6844* (2018.01)
*C12Q 1/6888* (2018.01)

(52) U.S. Cl.
CPC .......... *C12Q 1/6806* (2013.01); *C07D 307/60* (2013.01); *C12Q 1/6809* (2013.01); *C12Q 1/6846* (2013.01); *C12Q 1/6888* (2013.01); *C12Q 2527/125* (2013.01)

(58) Field of Classification Search
None
See application file for complete search history.

(56) References Cited

FOREIGN PATENT DOCUMENTS

CN    1150584 A    5/1997

*Primary Examiner* — Michelle S Horning
(74) *Attorney, Agent, or Firm* — Daniel E. Agnew; Eric Grant Lee

(57) ABSTRACT

The present invention provides inactivated microbes, methods of preparing and using the same, as well as compositions and kits containing the same. The inactivated microbes are useful in the formulation of internal control reagents for use in recombinant nucleic acid techniques, especially nucleic acid amplification, e.g., by the polymerase chain reaction (PCR).

5 Claims, 6 Drawing Sheets

METHOD OF INACTIVATING MICROBES BY CITRACONIC ANHYDRIDE

CROSS REFERENCE TO RELATED APPLICATIONS

This patent application is a divisional patent application of U.S. patent application Ser. No. 15/569,361, filed Oct. 25, 2017, which is the national stage entry of International Patent Application No. PCT/EP2016/061705, filed May 24, 2016, which claims the benefit of priority of U.S. Provisional Patent Application No. 62/168,541, filed May 19, 2015, all of which are incorporated herein by reference in their entireties.

FIELD OF THE INVENTION

The present invention provides compositions of matter comprising an inactivated microbe suitable for use as a control in nucleic acid amplification detection methods.

BACKGROUND OF THE INVENTION

A reliable positive control is an important component of a molecular diagnostic test, particularly those tests which use nucleic acid amplification for the detection of microorganism(s). For instance, a reliable positive control provides confidence in the accuracy of a negative detection result of a microbe in a patient sample suspected of containing the microbe. Such a control may be an "internal control" or "IC", which is added to a portion of the sample tested in parallel for amplification and/or detection of the control nucleic acid target sequence while another portion of the sample is analyzed for amplification and/or detection of the target analyte nucleic acid sequence to be detected by the assay. An "internal control" is typically used where both control target nucleic acid sequences and analyte nucleic acid sequence are purified, amplified, and/or detected in the same reaction vessel (see, e.g., U.S. Pat. No. 7,718,402). A full process internal control, i.e., a control for all steps of an assay including sample handling, nucleic acid extraction, amplification, detection, etc., is an important component of a diagnostic test that utilizes nucleic acid amplification. Where a microbe is used as full process internal control, it is highly desirable (if not required to comply with certain regulatory guidelines) to be noninfectious (see, e.g., WO 2002/033129; U.S. 2002-0076773 A1).

Certain compounds have been used to reversibly inactivate thermostable polymerases, including formaldehyde, dicarboxylic acid anhydride, and citraconic anhydride (see, e.g., U.S. Pat. Nos. 6,183,998; 6,479,264; and 7,972,830). There is a need for new compositions of matter comprising inactivated microbes, and methods of preparing and using the same.

The present invention provides methods of inactivating a microbe containing a target nucleic acid sequence with citraconic anhydride while preserving the integrity of the target nucleic acid sequence, as well as inactivated microbes prepared using such methods.

BRIEF SUMMARY OF THE INVENTION

The present invention provides inactivated microbes, methods of preparing and using the same, as well as compositions and kits containing the same. The inactivated microbes are useful in the formulation of internal control reagents for use in recombinant nucleic acid techniques, especially nucleic acid amplification, e.g., by the polymerase chain reaction (PCR).

In one aspect, the present invention provides methods for exogenous inactivation of a microbe. In one embodiment, the method comprises exogenously contacting an infectious microbe with citraconic anhydride. In some embodiments, the microbe comprises a control nucleic acid sequence. In some embodiments, the citraconic anhydride is an effective amount of citraconic anhydride. In some embodiments, contacting the microbe inactivates the microbe while preserving the integrity of the control nucleic acid sequence. In one embodiment, a method for exogenous inactivation of a microbe is provided comprising exogenously contacting an infectious microbe containing a control nucleic acid sequence with an effective amount of citraconic anhydride, thereby inactivating the microbe while preserving the integrity of the control nucleic acid sequence. In certain embodiments, the effective amount of citraconic anhydride is (i) at a concentration between about 5 mM and about 25 mM; (ii) at a concentration between about 5.5 mM and about 22 mM or (iii) at a concentration selected from the group consisting of about 5.5 mM, about 11 mM, and about 22 mM. In one embodiment, the microbe prior to the contacting step comprises a proteinaceous outer surface comprising at least one primary amine group. In another embodiment, the inactivated microbe comprises a proteinaceous outer surface comprising at least one modified primary amine group. In one embodiment, the at least one modified primary amine group is modified to an amide linkage and a terminal carboxylate. In certain embodiments, the inactivated microbe comprises a proteinaceous outer surface comprising at least one primary amine group modified to an amide linkage and a terminal carboxylate. In other embodiments, the contacting step is performed at ambient temperature, and/or the contacting is performed for about 1 hour. In certain embodiments, the microbe is a virus, more specifically an RNA or DNA virus. In other embodiments, the microbe is an armored nucleic acid, more specifically an armored RNA or DNA. In another embodiment, the microbe is selected from the group consisting of a virus, an RNA virus, a DNA virus, an armored nucleic acid, an armored RNA or DNA, and a bacteriophage.

In one other aspect, the present invention provides a method of verifying a detection result for a test sample in a nucleic acid amplification assay. In one embodiment, the method comprises performing sample preparation on a mixture comprising a test sample and an inactivated microbe, wherein the inactivated microbe comprises (i) a control nucleic acid sequence; and (ii) a proteinaceous outer surface having at least one primary amine group modified to an amide linkage and a terminal carboxylate, wherein the sample preparation releases nucleic acid from both the test sample and the inactivated microbe. The method further comprises the steps of performing nucleic acid amplification on the released nucleic acid detecting said control nucleic acid target, thereby verifying the detection result.

In a further aspect, the present invention provides sample preparation mixtures comprising an inactivated microbe. In one embodiment, the mixture comprises an inactivated microbe with a proteinaceous outer surface comprising at least one primary amine group modified to an amide linkage and a terminal carboxylate. Herein, the mixture further comprises a sample preparation reagent. In certain embodiments, the sample preparation reagent is a protease. In certain embodiments, the sample preparation reagent is a solid support material. In certain embodiments, the sample preparation reagent is a lysis buffer. In another embodiment, the sample preparation reagent is selected from the group consisting of a protease, a solid support material, and a lysis buffer. In certain embodiments, the microbe is selected from the group consisting of a virus, an RNA or DNA virus, an armored nucleic acid, an armored RNA or DNA, and a bacteriophage.

In another aspect, the present invention provides microbe inactivation reaction mixtures comprising a microbe. In one embodiment, the mixture comprises a microbe with a proteinaceous outer surface, a reaction buffer, and an effective amount of citrconic anhydride. In certain embodiments, the effective amount of citraconic anhydride is (i) at a concentration between about 5 mM and about 25 mM; or (ii) at a concentration selected from the group consisting of about 5.5 mM, about 11 mM, and about 22 mM. In one embodiment, the microbe comprises a proteinaceous outer surface comprising at least one primary amine group. In certain embodiments, the microbe is a virus, more specifically an RNA or DNA virus. In other embodiments, the microbe is an armored nucleic acid, more specifically an armored RNA or DNA. In another embodiment, the microbe inactivation reaction mixture comprises a microbe selected from the group consisting of a virus, an RNA virus, a DNA virus, an armored nucleic acid, an armored RNA, an armored DNA, and a bacteriophage.

BRIEF DESCRIPTION OF THE DRAWINGS

FIG. 6A depicts the reaction of citraconic anhydride with a primary amine at different pHs. FIG. 6B depicts the reaction of citraconic anhydride with a primary amine at a certain pH to form an amide linkage (dashed line oval) and a terminal carboxylate (solid line oval).

DEFINITIONS

Figure 1:
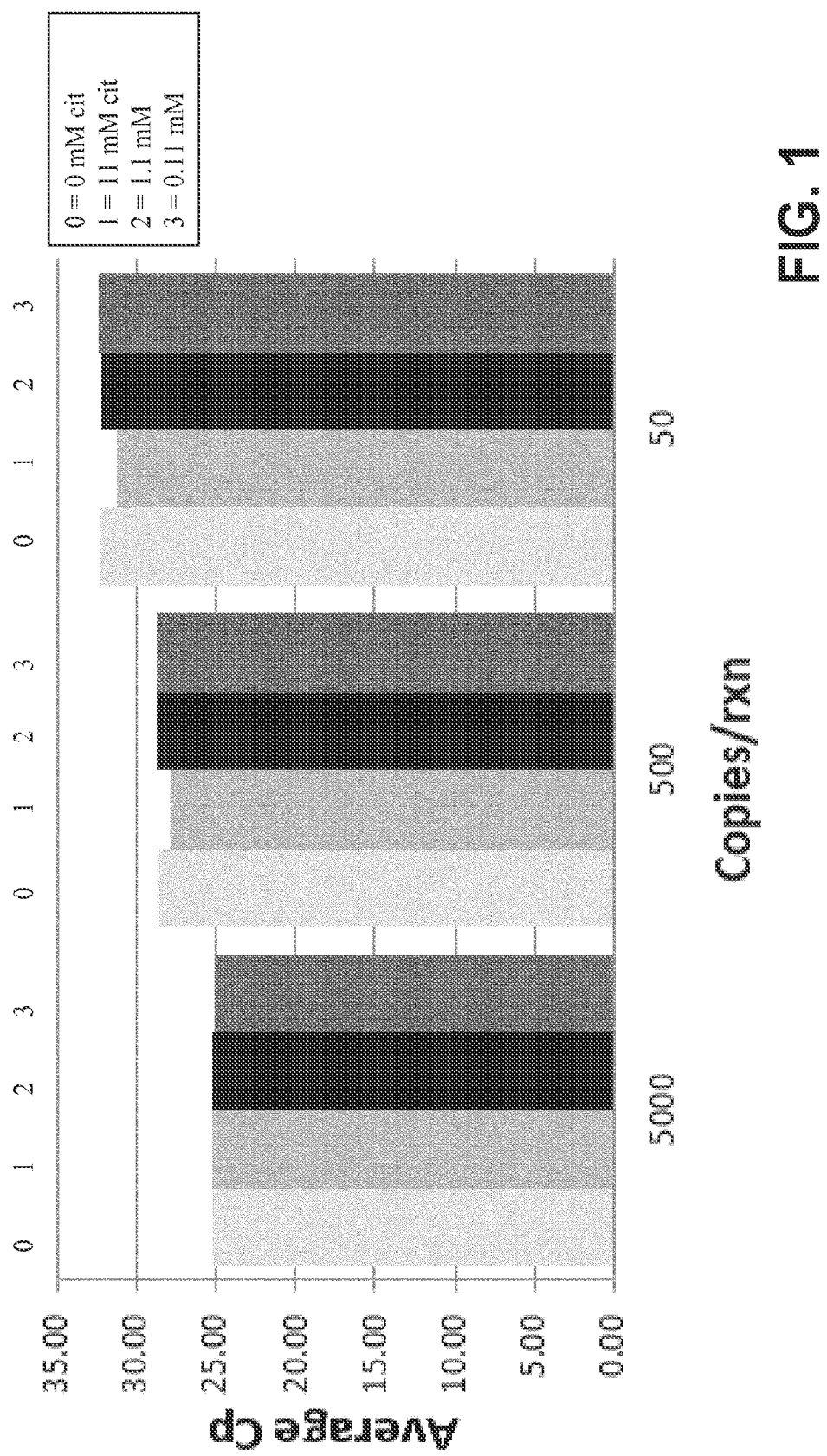
FIG. 1 shows the results of nucleic acid amplification from citraconic anhydride-inactivated bacteriophage.

Unless defined otherwise, all technical and scientific terms used herein have the same meaning as commonly understood by one of ordinary skill in the art to which this disclosure pertains. Although essentially any methods and materials similar to those described herein can be used in the practice or testing of the present disclosure, only exemplary methods and materials are described. For purposes of the present disclosure, the following terms are defined below.

The terms "a," "an," and "the" include plural referents, unless the context clearly indicates otherwise.

The term "about" encompasses variations of the indicated value of +/−15%, +/−10%, +/−5%, +/−3%, +/−2% or +/−1% and the indicated value itself.

The term "microbe" refers to an infectious agent that has the ability to infect a host including, without limitation, a bacterial host. The microbes contemplated herein possess a proteinaceous outer surface that plays a role in facilitating host infection. An example of a microbe is a virus including, without limitation, an RNA virus and a DNA virus. Microbes also include bacteriophages.

The term "virus", "virion", and "viral particle" are used herein interchangeably. A virus is a submicroscopic infectious agent that is unable to grow or reproduce outside a host cell. Each virus consists of genetic material, DNA or RNA, within a protective protein coat called a capsid. The capsid shape varies from simple helical and icoshedral (polyhedral or near-spherical) forms, to more complex structures with tails or an envelope. Viruses infect cellular life forms including without limitation bacterial types, according to the type of host infected. The present disclosure applies to different viruses including, without limitation, bacteriophages, wild-type viruses, attenuated viruses, empty virus particles as well as genetically modified viral vectors which can either be replication competent or incompetent.

The term "bacteriophage" as used herein is a virus that infects a bacterium. In one embodiment, the bacterium is of a type which causes an infective disease. The bacteriophage may (i) constitute a single or double-stranded DNA or RNA virus; and/or (ii) be enveloped or non-enveloped. Those of ordinary skill in the art will appreciate that a suitable bacteriophage can be selected from any taxonomic family, subfamily, genus or species.

The term "host cell" refers to both single-cellular prokaryote and eukaryote organisms (e.g., bacteria, yeast, and actinomycetes) and single cells from higher order plants or animals when being grown in cell culture. In the context of the present disclosure, the host cell is infected with and/or comprises a microbe, e.g., a virus or bacteriophage.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymeras chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The terms "peptide," "polypeptide," and "protein" are used interchangeably. The terms "nucleic acid" and "polynucleotide" are used interchangeably. Amino acid sequences are written from amino terminus to carboxy terminus, unless otherwise indicated. Single-stranded nucleic acid sequences are written 5' to 3', unless otherwise indicated. The top strand of a double-stranded nucleic acid sequence is written 5' to 3', and the bottom strand is written 3' to 5', unless otherwise indicated.

The term "armored" particle refers to a nucleic acid particle subjected to substantial, partial, or complete encapsulation within a structure composed of viral coat proteins. As described in U.S. Pat. Nos. 5,677,124 and 5,939,262, armored particles may be produced heterologously. For example, RNA may be transcribed in vivo in a bacterial host and at least partially encapsulated by bacteriophage proteins, which renders the RNA resistant to nuclease or ribonuclease degradation.

"Exogenous" in the context of the present disclosure means that the agents for microbe inactivation are contacted with isolated microbes in an appropriate buffer that will allow the inactivation to occur. The presence of a cellular host is not necessary for the process/technology.

Figure 6A:
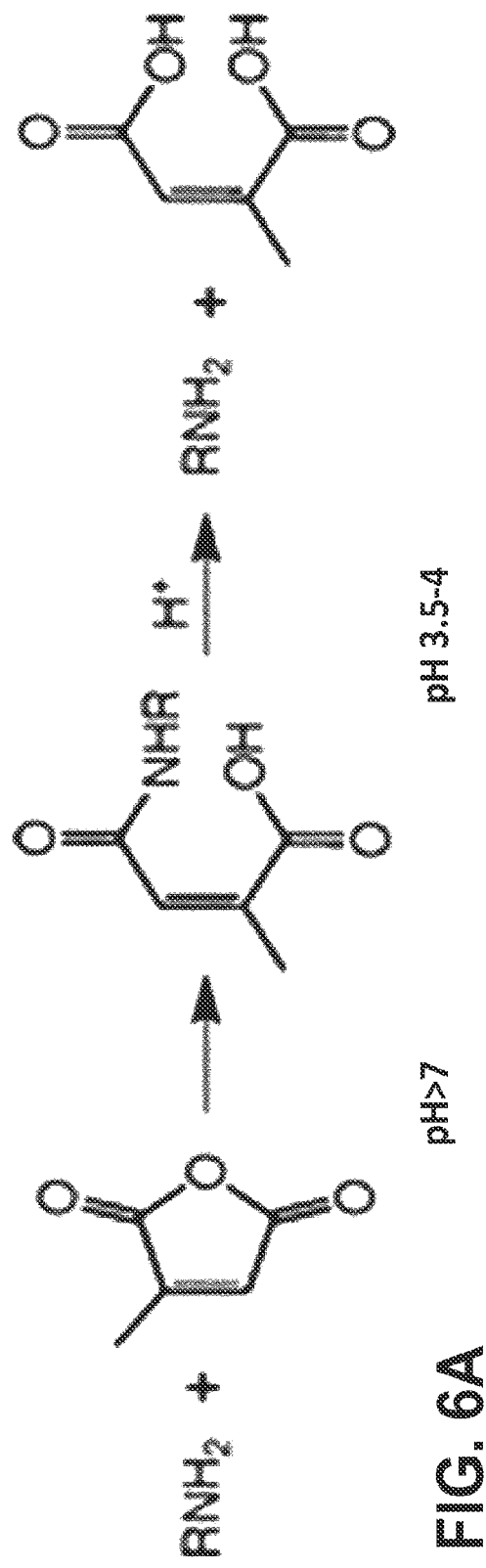
FIG. 6A-B illustrates the modification of a primary amine group to an amide linkage and a terminal carboxylate.
Figure 6B:
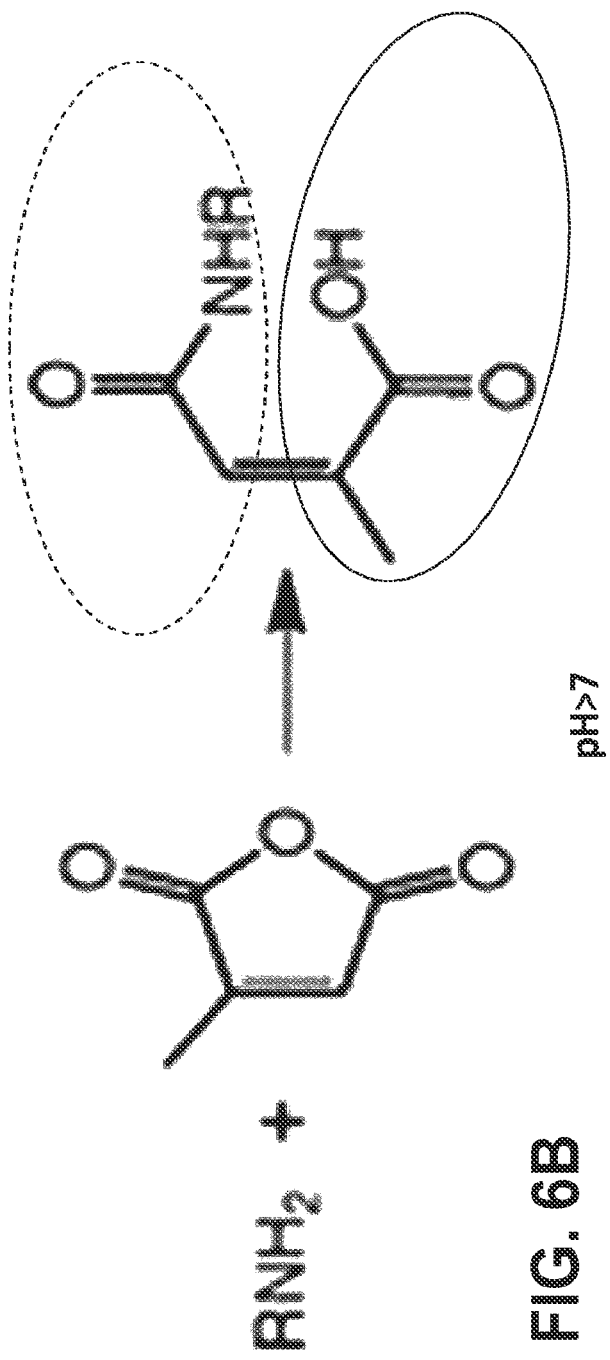

The term "proteinaceous outer surface" refers to an outer surface of a microbe that encompasses amino molecule sequences comprising at least one of the 20 common amino acids in naturally synthesized proteins. For example, following inactivation according to the present disclosure, the proteinaceous outer surface comprises at least one modified amino acid, e.g., an amino acid having a modified primary amine as shown in FIG. 6A-B.

The term "Cp value" or "crossing point" value refers to a value that allows quantification of input target nucleic acids. The Cp value can be determined according to the second-derivative maximum method (Van Luu-The, et al., "Improved real-time RT-PCR method for high-throughput measurements using second derivative calculation and double correction," BioTechniques, Vol. 38, No. 2, February 2005, pp. 287-293). In the second derivative method, a Cp corresponds to the first peak of a second derivative curve. This peak corresponds to the beginning of a log-linear phase. The second derivative method calculates a second derivative value of the real-time fluorescence intensity curve, and only one value is obtained. The original Cp method is based on a locally defined, differentiable approximation of the intensity values, e.g., by a polynomial function. Then the third derivative is computed. The Cp value is the smallest root of the third derivative. The Cp can also be determined using the fit point method, in which the Cp is determined by the intersection of a parallel to the threshold line in the log-linear region (Van Luu-The, et al., BioTechniques, Vol. 38, No. 2, February 2005, pp. 287-293). The Cp value provided by the LightCycler instrument offered by Roche by calculation according to the second-derivative maximum method.

The term "PCR efficiency" refers to an indication of cycle to cycle amplification efficiency. PCR efficiency is calculated for each condition using the equation: % PCR efficiency=$(10^{(-slope)}-1) \times 100$, wherein the slope was calculated by linear regression with the log copy number plotted on the y-axis and Cp plotted on the x-axis. PCR efficiency can be measured using a perfectly matched or mismatched primer template.

The term "nucleic acid extension rate" refers the rate at which a biocatalyst (e.g., an enzyme, such as a polymerase, ligase, or the like) extends a nucleic acid (e.g., a primer or other oligonucleotide) in a template-dependent or template-independent manner by attaching (e.g., covalently) one or more nucleotides to the nucleic acid.

The term "5'-nuclease probe" refers to an oligonucleotide that comprises at least one light emitting labeling moiety and that is used in a 5'-nuclease reaction to effect target nucleic acid detection. In some embodiments, for example, a 5'-nuclease probe includes only a single light emitting moiety (e.g., a fluorescent dye, etc.). In certain embodiments, 5'-nuclease probes include regions of self-complementarity such that the probes are capable of forming hairpin structures under selected conditions. To further illustrate, in some embodiments a 5'-nuclease probe comprises at least two labeling moieties and emits radiation of increased intensity after one of the two labels is cleaved or otherwise separated from the oligonucleotide. In certain embodiments, a 5'-nuclease probe is labeled with two different fluorescent dyes, e.g., a 5' terminus reporter dye and the 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched at least in part. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission of the reporter dye is no longer quenched. Exemplary 5'-nuclease probes are also described in, e.g., U.S. Pat. Nos. 5,210,015, 5,994,056, and 6,171,785. In other embodiments, a 5' nuclease probe may be labeled with two or more different reporter dyes and a 3' terminus quencher dye or moiety.

The term "FRET" or "fluorescent resonance energy transfer" or "Foerster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™ (Integrated DNA Tech., Inc., Coralville, Iowa), and BlackBerry™ Quencher 650 (BBQ-650) (Berry & Assoc., Dexter, Mich.).

DETAILED DESCRIPTION OF THE INVENTION

The present invention provides inactivated microbes, methods of preparing and using the same, as well as compositions and kits containing the same. The inactivated microbes are useful in the formulation of internal control reagents for use in recombinant nucleic acid techniques, especially nucleic acid amplification, e.g., by the polymerase chain reaction (PCR). In particular, the present invention provides an inactivated or non-infectious microbe which contains a target nucleic acid sequence that can be used as an internal control to verify a detection result from nucleic acid amplification.

Inactivated Microbes

Microbes are typically characterized by a proteinaceous outer surface that serves among other things to protect an RNA or DNA genome. For example, a bacteriophage has an outer surface comprising predominantly proteins that not only encapsulate a genome but also provide the machinery by which the phage infects a host cell to replicate. The outer surface of a virus typically contains glycoproteins that help facilitate attachment to the surface of a host cell and subsequent injection of genetic material.

According to the present disclosure, an inactivated microbe comprises a modified proteinaceous outer surface having at least one primary amine group. In one embodiment, the at least one primary amine group is a lysine primary amine group. In one other embodiment, the primary amine group is a modified primary amine group. In another embodiment, the modified primary amine group is modified to an amide linkage and a terminal carboxylate. In one additional embodiment, the inactivated microbe is a derivatized microbe with a proteinaceous outer surface comprising at least one primary amine group modified to an amide linkage and a terminal carboxylate. In some embodiments, the derivatized microbe is a virus including, without limitation, a bacteriophage. In other embodiments, the derivatized microbe is an RNA or DNA virus. In one other embodiment, the derivatized microbe is an armored nucleic acid including, without limitation, an armored RNA or DNA.

The present disclosure provides "altered", "modified", "inactivated", or "derivatized" microbes. These terms in the context of the present disclosure are used interchangeably and refer to a microbe having a proteinaceous outer surface wherein the composition of the outer surface comprises a primary amine group modified to an amide linkage and a terminal carboxylate. FIG. 6A-B illustrates the modification of a primary amine group to an amide linkage and a terminal carboxylate. FIG. 6A-B depicts the terminal carboxylate in the form of a carboxylic acid having a hydroxyl group. However, it will be appreciated by those of ordinary skill in the art that the terminal carboxylate according to the present disclosure is the result of the dissociation of carboxylic acid into a carboxylate anion and a positively charged hydrogen ion. As shown below, the negative charge of the carboxylate ion following deprotonation is delocalized between the two electronegative oxygen atoms in a stable resonance structure.

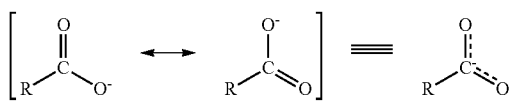

In one embodiment, the microbe is a virus that has been modified as per the methods of the present disclosure after release of the viral particles from its respective host cell, preferably after isolation and concentration of intact viral particles from their natural environment or a technical production process. The modification of the composition of a virus protein can be used to modify the chemical and/or biological characteristics of a virus particle. For example, the ability of the virus to attach to a host cell and inject its genetic material can be adjusted, thereby modifying the infectivity of the virions.

In another aspect, the microbes inactivated by the methods of the present disclosure remain in an inactivated state following treatment with citraconic anhydride as per the methods described herein. The inactivation state may be verified or tested by methods known to those of ordinary skill in the art. In one embodiment, the inactivation state is verified by testing the ability of the inactivated microbe to propagate itself. In the case of an inactivated virus, the state of inactivation can be tested by measuring the ability of the virus to form plaques in a host cell monolayer. A plaque-forming unit (PFU) is a measure of the number of particles capable of forming plaques per unit volume, such as virus particles. The measure of pfu/mL is a well accepted functional measurement of the ability of viral particles to infect host cells. Viral particles that are defective or which fail to infect their target host cell, i.e., inactivated viral particles, will not produce a plaque and thus will not be counted. In one embodiment, the inactivated microbes of the present disclosure remain inactivated for at least one month following inactivation by the methods of the present disclosure. In a particular embodiment, the inactivated microbe is an inactivated virus.

In one aspect, the inactivated microbe of the present disclosure contains a control target nucleic acid sequence. Control target nucleic acids can come from a biological or synthetic source. The target can be, for example, DNA or RNA. Generally, where amplicons are generated, the amplicons will be composed of DNA, though ribonucleotides or synthetic nucleotides can also be incorporated into the amplicon. When it is necessary to detect an RNA virus, the amplification process will typically involve the use of reverse transcription, including for example, reverse transcription PCR (RT-PCR).

The disclosure provides embodiments wherein the internal control nucleic acid is DNA, wherein the internal control nucleic acid is RNA, and further, wherein the internal control nucleic acid is an armored nucleic acid. Since RNA is more prone to degradation than DNA due to influences such as alkaline pH, ribonucleases etc., internal control nucleic acids made of RNA may be provided as armored particles. Armored particles such as especially armored RNA are described e.g. in U.S. Pat. No. 6,214,982. In brief, the RNA, which can be produced chemically or heterologously e.g. by bacteria such as e.g. E. coli, is at least partially encapsulated in a viral coat protein. The latter confers resistance of the RNA towards external influences, in particular ribonucleases. It must be understood that internal control DNA can also be provided as an armored particle. Both armored RNA and DNA are useful as internal control nucleic acids in the context of the disclosure. In an embodiment, RNA control nucleic acids are armored with the MS2 coat protein in E. coli. In a further embodiment, DNA control nucleic acids are armored using lambda phage GT11.

Further, the disclosure provides embodiments wherein the sequence of the internal control nucleic acid is different from the sequences of the other nucleic acids present in the one or more samples, wherein the sequence of the internal control nucleic acid is derived from a naturally occurring genome, wherein the sequence of the internal control nucleic acid is scrambled, and wherein the internal control nucleic acid has a melting temperature from about 50° C. to about 90° C. The internal control nucleic acid may be of any suitable length. Preferably, the sequence of the internal control nucleic acid has different primer binding sites than the target and thus binds to different primers. Advantages of such a strategy comprise, among others, the fact that the single amplification events of the different nucleic acids in the reaction mixture can take place independently from each other without any competition effects. For such a setup, the internal control nucleic acid has a sequence different from any target sequences, in order not to compete for their primers and/or probes. For example, the sequence of the internal control nucleic acid can be different from the other nucleic acid sequences in the fluid sample. As an example, if the fluid sample is derived from a human, the internal control nucleic acid may not have a sequence which also endogenously occurs within humans. The difference in sequence should thus be at least significant enough to not allow the binding of primers and/or probes to the respective endogenous nucleic acid or acids under stringent conditions and thus render the setup competitive. In order to avoid such interference, the sequence of the internal control nucleic acid used in the disclosure can be derived from a source different from the origin of the fluid sample. For example, it is derived from a naturally occurring genome, for example a plant genome, or from a grape genome. In an embodiment, a nucleic acid derived from a naturally occurring genome is scrambled. As known in the art, "scrambling" means introducing base mutations in a sequence to a certain extent. For example, the sequence of the internal control nucleic acid used in the disclosure is substantially altered with respect to the naturally occurring gene it is derived from.

In another aspect, the present disclosure provides an inactivation reaction mixture, and an inactivation reaction vessel, wherein the mixture or vessel comprises a microbe i.e., a microbe that has not been inactivated. In one embodiment, the present disclosure provides an inactivation reaction mixture comprising a microbe, a buffer, and citraconic anhydride.

In another embodiment, the citraconic anhydride is an effective amount of citraconic anhydride. In another embodiment, the present disclosure provides an inactivation reaction vessel for microbe inactivation comprising a microbe, a buffer, and citraconic anhydride.

In some embodiments, the buffer for use in an inactivation reaction mixture or vessel is SM buffer (0.1 M NaCl, 10 mM MgSO4, 50 mM Tris pH 7.5, 0.01% gelatin) as described in the Examples section herein. In one other embodiment, an inactivation reaction vessel is a container in which the inactivation reaction between a microbe and citraconic anhydride takes place. In one additional embodiment, an inactivation reaction mixture is a mixture that allows the inactivation reaction between a microbe and citraconic anhydride to take place.

As described herein, the inactivated microbes of the present disclosure are useful in the formulation of internal control reagents for nucleic acid amplification. In one additional aspect, the present disclosure provides assay reaction mixtures and assay reaction vessels comprising inactivated microbes as described herein, wherein such mixtures and vessels may find use in the steps preceding transcription and amplification of nucleic acid. Sample preparation occurs prior to transcription and amplification so the assay reaction mixture may be referred to as a sample preparation mixture and the assay reaction vessel may be referred to as a sample preparation vessel. In one aspect, the present disclosure contemplates different assay reagents including, without limitation, assay reagents involved in sample preparation. The assay reagents may also be referred to as "sample preparation" reagents. For instance, to release the contents of microbes they may be treated with enzymes or with chemicals to dissolve, degrade or denature the proteinaceous outer surface of a microbe. This process is commonly referred to as lysis. The resulting solution containing such lysed material is referred to as lysate. In one embodiment, the present disclosure provides an assay reaction mixture comprising a derivatized microbe with a proteinaceous outer surface comprising at least one primary amine group modified to an amide linkage and a terminal carboxylate, and an assay reagent.

In one embodiment, the present disclosure provides a reaction mixture comprising a derivatized microbe with a proteinaceous outer surface comprising at least one primary amine group modified to an amide linkage and a terminal carboxylate, and an assay reagent (or sample preparation reagent). In another embodiment, the assay reagent is used in a step that precedes the transcription and amplification steps of nucleic acid amplification. In one embodiment, the reaction mixture further comprises a biological sample, e.g., a patient sample, suspected of containing a target nucleic acid sequence. In such cases, the inactivated microbe will serve as the internal positive control to verify a nucleic acid detection result. In one embodiment, the assay reagent is selected from the group consisting of a protease, a solid support material, and a lysis buffer.

In an additional embodiment, the assay reagent is a lysis buffer. A suitable lysis buffer comprises one or more components selected from the group consisting of: a chaotropic agent, a buffer substance, an alcohol, and a reducing agent. Chaotropic agents generally disturb the ordered structure of water molecules in solution and non-covalent binding forces in and between molecules, and such agents can make several contributions to the procedure of sample preparation. In particular, but not only, they can be applied as RNase inhibitors by disturbing the nuclease's tertiary structure. Usually, no further RNase inhibitor has to be applied to the lysis buffer. Also, they can play a significant role in the adhesive binding of nucleic acids to surfaces like glass. Exemplary chaotropic agents in the context of the disclosure are guanidinium salts like guanidinium thiocyanate or guanidinium hydrochloride or guanidinium chloride or guanidinium isothiocyanate, urea, perchlorates such as e.g. potassium perchlorate, other thiocyanates or potassium iodide. However, other chaotropic agents can also be used. Buffer substances are generally important for maintaining a certain pH value or pH range in a solution. This is the prerequisite for most biological systems, and mostly also desirable for in vitro reactions. It can also be advantageous for use with the inactivated microbes of the present disclosure. Exemplary buffers in the context of the disclosure are citrate buffers such as sodium citrate, but also Tris(Tris-(hydroxymethyl)-aminomethane) buffers such as Tris HCl, phosphate, N-(2-hydroxyethyl)-piperazine-N'-(2-ethanesulfonic acid) (HEPES), acetate buffers, but also other buffers can be used in the context of the disclosure. The use of alcohol in a lysis buffer for nucleic acid preparation can also be advantageous, as known by the person skilled in the art. An example in the context of the disclosure is the use of polidocanol, while other alcohol may also be used in the lysis buffer described above. The use of polidocanol for the preparation of nucleic acids has, e.g., been described in EP 1932 913. Reducing agents can also contribute to the denaturation of undesired components such as the RNase A mentioned above. In particular, reducing agents, as widely known in the art, cleave inter- and intramolecular disulfide bonds, which are especially important for the tertiary structure of many proteins. An example in the context of the disclosure is a reducing agent such as dithiothreitol (DTT). Other reducing agents known in the art such as, e.g., 2-mercaptoethanol can also be advantageously employed in the context of the disclosure.

In some alternative embodiment, the assay reaction mixtures and/or assay reaction vessels of the present disclosure explicitly exclude or lack a reducing agent. Such assay reaction mixtures and/or assay reaction vessels are provided without a reducing agent and/or are characterized by an absence of a reducing agent.

In view of the aforementioned, an aspect of the disclosure is the process described above, wherein said lysis buffer comprises the following components: Guanidinium thiocyanate, NaCitrate, polydocanol, and DTT. In an embodiment of the disclosure, the concentrations of the above-mentioned components of the lysis buffer are as follows Guanidinium thiocyanate: 4 M, NaCitrate: 50 mM, polydocanol: 5% w/v, and DTT: 2% w/v (see U.S. Published Patent Application No. 20120045751). The pH of the lysis buffer described above is not restricted to specific pH values. However, in an embodiment, said lysis buffer has an acidic pH, or a pH between 5.5 and 6.5, or about 5.8.

In another embodiment, the assay reagent is a protease. It is advantageous to use proteases which rapidly degrade the previously described enzymes or unwanted proteins. However, this may produce another problem as said substances or enzymes can interfere with reagents or components in subsequent steps. Enzymes which can be used in such lysis or sample preparation processes mentioned above are enzymes which cleave the amide linkages in protein substrates and which are classified as proteases, or (interchangeably) peptidases (see Walsh, 1979, Enzymatic Reaction Mechanisms. W. H. Freeman and Company, San Francisco, Chapter 3). Suitable proteases include, without limitation, alkaline proteases (WO 98/04730) or acid proteases (U.S. Pat. No. 5,386,024). A protease which has been widely used for sample preparation in the isolation of nucleic acids in the prior art is proteinase K from Tritirachium album (see e.g. Sambrook J. et al., Molecular Cloning: A Laboratory Manual, Cold Spring Harbor Laboratory Press, Cold Spring Harbor, N.Y., 1989) which is active around neutral pH and belongs to a family of proteases known to the person skilled in the art as subtilisins. An example for the use in lysis or sample preparation processes mentioned above is the enzyme esperase, a robust protease that retains its activity at both high alkalinity and at high temperatures (EP 1 201 753).

In another embodiment, the assay reagent is a solid support material. In the present disclosure, a solid support material is combined together with an inactivated microbe (e.g., before or after lysis). The term "solid support material" comprises any of the solid materials mentioned above in connection with the immobilization of nucleic acids, e.g. magnetic glass particles, glass fibers, glass fiber filters, filter paper etc., while the solid support material is not limited to these materials. In one embodiment, the solid support material is combined after lysis for a period of time and under conditions sufficient to permit nucleic acids released from the inactivated microbe to be immobilized on the solid support material. In a preferred embodiment, the nucleic acids comprise a control nucleic acid sequence. The solid support material is then isolated from the other material present, and the nucleic acids are purified by separating remainder from the solid support material and washing the solid support material one or more times with a wash buffer. In the sense of the disclosure, "purification", "isolation" or "extraction" of nucleic acids relate to the following: Before nucleic acids may be analyzed in a diagnostic assay e.g. by amplification, they typically have to be purified, isolated or extracted from an internal control reagent (and from the corresponding biological sample, which may contain complex mixtures of different components). For these first steps, processes may be used which allow the enrichment of the nucleic acids.

One aspect of the disclosure is the process described above, wherein the solid support material comprises nucleic acid binding particles, or one or more of the materials selected from silica, metal, metal oxides, plastic, polymers and nucleic acids. In one embodiment of the disclosure, the solid support material is magnetic glass particles.

"Immobilize", in the context of the disclosure, means to capture objects such as e.g. nucleic acids in a reversible or irreversible manner. Particularly, "immobilized on the solid support material", means that the object or objects are associated with the solid support material for the purpose of their separation from any surrounding media, and can be recovered e.g. by separation from the solid support material at a later point. In this context, "immobilization" can e.g. comprise the adsorption of nucleic acids to glass or other suitable surfaces of solid materials as described supra. Moreover, nucleic acids can be "immobilized" specifically by binding to capture probes, wherein nucleic acids are bound to essentially complementary nucleic acids attached to a solid support by base-pairing. In the latter case, such specific immobilization leads to the predominant binding of target nucleic acids.

In a further aspect of the disclosure, the use of citraconic anhydride for exogenous inactivation of a microbe is disclosed, whereby the microbe is inactivated while preserving the integrity of the control nucleic acid sequence. Herein, an effective amount of citraconic anhydride is to be applied to the microbe. In certain embodiments, said microbe comprises a proteinaceous outer surface comprising at least one primary amine group prior to being in contact with the effective amount of citraconic anhydride. In certain embodiments, after inactivation the microbe comprises a proteinaceous outer surface comprising at least one primary amine group modified to an amide linkage and a terminal carboxylate. An "effective amount" of citraconic anhydride refers to the amount sufficient to inactivate a microbe. For instance, sufficient microbe inactivation can be confirmed according to the protocols described herein or otherwise described in the art. In one embodiment, the effective amount of citraconic anhydride is at a concentration between about 5 mM and about 25 mM, between about 1 mM and about 7 mM, between about 5 mM and about 15 mM, and about 11 mM and about 22 mM. In other embodiments, the effective amount is about 1 mM, about 2 mM, about 3 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, about 10 mM, about 10.5 mM, about 11 mM, about 11.5 mM, about 12 mM, about 12.5 mM, about 13 mM, about 13.5 mM, about 14 mM, about 15 mM, about 16 mM, about 17 mM, about 18 mM, about 19 mM, about 19.5 mM, about 20 mM, about 20.5 mM, about 21 mM, about 21.5 mM, about 22 mM, about 22.5 mM, about 23 mM, about 24 mM, and about 25 mM. In some embodiments, the effective amount of citraconic anhydride is (i) at a concentration between about 5 mM and about 25 mM; (ii) at a concentration between about 5.5 mM and about 22 mM or (iii) at a concentration selected from the group consisting of about 5.5 mM, about 11 mM, and about 22 mM. In some embodiments, the microbe is contacted with citraconic anhydride at ambient temperature and/or for about 1 hour. In some embodiments, the microbe is a virus, more specifically an RNA or DNA virus. In some embodiments, the microbe is an armored nucleic acid, more specifically an armored RNA or DNA Methods of Inactivating Microbes In one aspect, the present disclosure provides methods of inactivating a microbe. In one embodiment, the method includes the step of providing in a liquid matrix an infectious microbe containing a control nucleic acid sequence. In another embodiment, the method also includes the step of contacting the microbe with an effective amount of citraconic anhydride. In one other embodiment, the method inactivates the microbe while preserving the integrity of the control nucleic acid sequence. In the present disclosure, preserving the integrity of the control nucleic acid sequence means that the sequence is not damaged or compromised due to the citraconic anhydride treatment such that it cannot be used as an internal control reagent in a nucleic acid amplification reaction. The integrity of the sequence can be confirmed by standard techniques known to those of ordinary skill in the art.

In one other aspect, the microbe inactivation method of the present disclosure is a method of exogenous modification of a microbe. For instance, citraconic anhydride is exogenously contacted with an isolated microbe in an appropriate buffer to allow modification (and inactivation) to occur. In one embodiment, the appropriate buffer is a liquid (or aqueous) matrix or suspension medium like buffered saline or a physiological saline. In one other embodiment, the suspension fluid is Tris-buffered saline or a buffer that comprises tricine.

In a preferred embodiment, the microbe is a virus. In one embodiment, the method includes the step of concentrating isolated viral particles from a suspension fluid prior to or after treatment with citraconic anhydride. In another embodiment, the method also includes the step of contacting or incubating the concentrated viral particles with citraconic anhydride such that the viral particles are modified. In one additional embodiment, the method includes the step of separating the modified viral particles from excessive citraconic anhydride. In other embodiments, the concentration of isolated viral particles and/or separation of modified viral particles is achieved by ultracentrifugation, ultrafiltration, chromatography, or affinity chromatography. In a further embodiment, the method includes the step of detecting the modified viral particles. In other embodiments, the method includes the step of verifying the inactivation state of the modified viral particles, such as by measuring pfu/mL.

In another aspect, the present invention provides a method of inactivating a microbe by using an effective amount of citraconic anhydride. An "effective amount" of citraconic anhydride refers to the amount sufficient to inactivate a microbe. For instance, sufficient microbe inactivation can be confirmed according to the protocols described herein or otherwise described in the art. In one embodiment, the effective amount of citraconic anhydride is at a concentration between about 5 mM and about 25 mM, between about 1 mM and about 7 mM, between about 5 mM and about 15 mM, and about 11 mM and about 22 mM. In other embodiments, the effective amount is about 1 mM, about 2 mM, about 3 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, about 10 mM, about 10.5 mM, about 11 mM, about 11.5 mM, about 12 mM, about 12.5 mM, about 13 mM, about 13.5 mM, about 14 mM, about 15 mM, about 16 mM, about 17 mM, about 18 mM, about 19 mM, about 19.5 mM, about 20 mM, about 20.5 mM, about 21 mM, about 21.5 mM, about 22 mM, about 22.5 mM, about 23 mM, about 24 mM, and about 25 mM. In other embodiments, the effective amount is more than 25 mM. In a preferred embodiment, the effective amount of citraconic anhydride is provided in Tris buffered saline at about 5 mM or above.

In one additional aspect, the present disclosure provides a method having a contacting or incubation step that is achieved by slow agitation in a suitable buffer as described herein. In one embodiment, the contacting or incubating is carried out at temperatures between about 20° C. and about 40° C. In one other embodiment, the temperature is preferably between about 25° C. and about 35° C. and/or the incubation time is between about 1 and about 3 hours. In other embodiments, the contacting or incubating step is performed for a period of time between about 30 minutes and 90 minutes. In another embodiment, the contacting or incubating step is performed for about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, or about 90 minutes. In a preferred embodiment, the contacting or incubating step is performed at room temperature or ambient temperature. Generally, room temperature or the ambient temperature is the temperature of a temperature-controlled environment. Room temperature or ambient temperature ranges from about 18° C. to about 30° C. In one embodiment, room temperature or ambient temperature is about 18° C., about 19° C., about 20° C., about 21° C., about 22° C., about 23° C., about 24° C., about 25° C., about 26° C., about 27° C., about 28° C., about 29° C., or about 30° C. In another embodiment, room temperature or ambient temperature is about 25° C. In other embodiments, the contacting or incubating step may be performed at about 4° C.

In another preferred embodiment, the contacting or incubating step is performed at room temperature or ambient temperature for about 60 minutes. In a preferred embodiment, room temperature or ambient temperature is about 25° C.

Methods of Verifying Detection Results

The inactivated microbes, as well as the methods of making and using the same, of the present disclosure may be used for any purpose in which such an inactivated microbe is necessary or desired. In one aspect, the present disclosure provides inactivated microbes suitable for use as a positive internal control in a method of polynucleotide extension (e.g., PCR) or nucleic acid amplification assay. For example, the positive internal control is processed along with a sample through the steps of sample preparation (nucleic acid extraction), reverse transcription of RNA (if required) to provide cDNA, amplification of DNA, and detection of the amplified DNA (see U.S. Pat. No. 8,609,340). In one embodiment, the inactivated microbe is an inactivated virus. In a preferred embodiment, the inactivated microbe is a bacteriophage.

In general, the inactivated microbes of the present disclosure are suitable for use in any nucleic acid amplification and detection method. Other nucleic acid amplification methods to be used in the context of the disclosure comprise the Ligase Chain Reaction (LCR) (Wu D. Y. and Wallace R. B., Genomics 4 (1989) 560-69; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2; U.S. Pat. No. 4,851,331), Recombinase Polymerase Amplification (RPA) method (see for example U.S. Pat. No. 7,485,428); Rolling Circle Amplification (RCA), (See for example, Fire and Xu, Proc. Natl. Acad Sci. USA 92:4641-4645 (1995); Lui, et al., J. Am. Chem. Soc. 118:1587-1594 (1996); Lizardi, et al., Nature Genetics 19:225-232 (1998), U.S. Pat. Nos. 5,714,320 and 6,235,502); Helicase Dependant Amplification (HDA), (see for example Vincent et al., EMBO Reports 5(8): 795-800 (2004); U.S. Pat. No. 7,282,328); Multiple Displacement Amplification (MDA) (See for example Dean et. al., Proc. Natl. Acad Sci. USA 99:5261-5266 (2002)); Self-sustained Sequence Replication (3SR) (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), loop-mediated isothermal amplification (LAMP) (U.S. Pat. No. 6,410,278; Notomi et al., Nucleic Acids Res. 2000 Jun. 15; 28(12): e63), and nucleic acid sequence based amplification (NASBA) (U.S. Pat. No. 5,130,238). Further, there are strand displacement amplification (SDA) (U.S. Pat. Nos. 5,455,166 and 5,470,723), transcription mediated amplification (TMA) (See for example, Guatelli eta., Proc. Natl. Acad. Sci. USA 87:1874-1878 (1990)), and Qb-amplification (for a review see e.g. Whelen A. C. and Persing D. H., Annu. Rev. Microbiol. 50 (1996) 349-373; Abramson R. D. and Myers T. W., Curr Opin Biotechnol 4 (1993) 41-47).

Accordingly, in another aspect of the disclosure, methods of polynucleotide extension (e.g., PCR) using the inactivated microbes are provided. Conditions suitable for polynucleotide extension are known in the art. (see, e.g., Sambrook et al., Molecular Cloning: A Laboratory Manual (Cold Spring Harbor Laboratory Press, New York, N.Y., 3rd ed. 2001; Ausubel et al., Short Protocols in Molecular Biology (4th ed., John Wiley & Sons 1999)). Generally, a primer is annealed, i.e., hybridized, to a target nucleic acid (in a sample and/or in a control) to form a primer-template complex. The primer-template complex is contacted with the DNA polymerase and nucleoside triphosphates in a suitable environment to permit the addition of one or more nucleotides to the 3' end of the primer, thereby producing an extended primer complementary to the target nucleic acid. The primer can include, e.g., one or more nucleotide analog(s). In addition, the nucleoside triphosphates can be conventional nucleotides, unconventional nucleotides (e.g., ribonucleotides or labeled nucleotides), or a mixture thereof. In some variations, the polynucleotide extension reaction comprises amplification of a target nucleic acid. Conditions suitable for nucleic acid amplification using a DNA polymerase and a primer pair are also known in the art (e.g., PCR amplification methods). (See, e.g., Sambrook et al., supra; Ausubel et al., supra; PCR Applications: Protocols for Functional Genomics (Innis et al. eds., Academic Press 1999). In other, non-mutually exclusive embodiments, the polynucleotide extension reaction comprises reverse transcription of an RNA template (e.g., RT-PCR).

In some embodiments, the inactivated microbes of the present disclosure are used in a reverse transcription reaction. In some embodiments, the reverse transcription reaction is carried out in a mixture containing the inactivated microbe, an RNA template, one or more primer(s), and a thermostable DNA polymerase of the disclosure. The reaction mixture typically contains all four standard deoxyribonucleoside triphosphates (dNTPs) and a buffer containing a divalent cation and a monovalent cation. Exemplary cations include, e.g., $Mg^{2+}$, although other cations, such as $Mn^{2+}$ or $Co^{2+}$ can activate DNA polymerases. In other embodiments, the reverse transcription reaction is carried out with a suitable thermo-active DNA polymerase.

In another aspect, the present disclosure provides a method for verifying a detection result for a test sample in a nucleic acid amplification assay. In one embodiment, the method includes the step of performing sample preparation on a mixture comprising a test sample and a derivatized microbe (e.g., a modified or altered microbe). In another embodiment, the derivatized microbe comprises (i) a control nucleic acid sequence; and (ii) a proteinaceous outer surface having at least one primary amine group modified to an amide linkage and a terminal carboxylate. In one other embodiment, the sample preparation releases nucleic acid from both the test sample and the derivatized microbe. In another embodiment, the sample preparation releases (or extracts) nucleic acid from both the test sample and the derivatized microbe. In other embodiments, the nucleic acid from the test sample comprises a target nucleic acid to be amplified (in the case of DNA) or reverse transcribed (in the case of RNA). In the case of RNA extraction, the method further comprises a reverse transcription step to provide cDNA for subsequent nucleic acid amplification. In another embodiment, the method includes the step of performing nucleic acid amplification on the nucleic acid released from the test sample and derivatized microbe. In one embodiment, the method includes the step of detecting said target nucleic acid (if present), as well as said control nucleic acid target, thereby verifying the detection result. In another embodiment, the detecting step includes hybridizing the amplified target nucleic acid with detectably labeled nucleic acid probes, and detecting the hybridized amplified target nucleic acid. The foregoing method steps are well known to those of ordinary skill in the art. Hybridization and detection can be accomplished by use of, for example, 5'-nuclease probes and detection of amplicons with FRET methodology. In a particularly preferred embodiment, the method can further comprise quantification of the target nucleic acid contained in the biological sample.

Other methods for detecting extension products or amplification products using the methods of verifying a detection result for a test sample described herein include the use of fluorescent double-stranded nucleotide binding dyes or fluorescent double-stranded nucleotide intercalating dyes. Examples of fluorescent double-stranded DNA binding dyes include SYBR-green (Molecular Probes). The double stranded DNA binding dyes can be used in conjunction with melting curve analysis to measure primer extension products and/or amplification products. The melting curve analysis can be performed on a real-time PCR instrument, such as the ABI 5700/7000 (96 well format) or ABI 7900 (384 well format) instrument with onboard software (SDS 2.1). Alternatively, the melting curve analysis can be performed as an end point analysis. Exemplary methods of melting point analysis are described in U.S. Publication No. 2006/0172324.

In other embodiments, the method includes the step of preparing a sample for testing by adding a biological sample to be tested for the presence of a pathogen to a composition that contains an inactivated microbe described herein. In one embodiment, the preparing step is performed prior to the sample preparation step.

In one aspect, the inactivated microbes are suitable for methods of verifying qualitative or quantitative detection results. Qualitative detection of a nucleic acid in a biological sample is crucial e.g. for recognizing an infection of an individual. Thereby, one important requirement for an assay for detection of a microbial infection is that false-negative or false-positive results be avoided, since such results would almost inevitably lead to severe consequences with regard to treatment of the respective patient. Thus, especially in PCR-based methods, a qualitative internal control nucleic acid is added to the detection mix. Said control is particularly important for confirming the validity of a test result: At least in the case of a negative result with regard to the respective target nucleic acid, the qualitative internal control reaction has to perform reactive within given settings, i.e. the qualitative internal control must be detected otherwise the test itself is considered to be inoperative. Thus, an aspect of the disclosure is the process described above, wherein the presence of an amplification product of said internal control nucleic acid is indicative of an amplification occurring in the reaction mixture even in the absence of amplification products for one or more of said target nucleic acids (U.S. Pat. No. 8,877,464).

In addition to qualitative detection of the presence or absence of a nucleic acid in a sample, it is often important to determine the quantity of said nucleic acid. As an example, stage and severity of a viral disease may be assessed on the basis of the viral load. Further, monitoring of any therapy requires information on the quantity of a pathogen present in an individual in order to evaluate the therapy's success. For a quantitative assay, it is necessary to introduce a quantitative standard nucleic acid serving as a reference for determining the absolute quantity of a target nucleic acid. Quantitation can be effectuated either by referencing to an external calibration or by implementing an internal quantitative standard. The use of an internal control nucleic acid added to the test reaction itself has certain advantages. When serving as a quantitative standard, said internal control nucleic acid has at least the following two functions in a quantitative test: i) it monitors the validity of the reaction. ii) it serves as reference in titer calculation thus compensating for effects of inhibition and controlling the preparation and amplification processes to allow a more accurate quantitation (U.S. Pat. No. 8,877,464).

Kits

In another aspect, the present disclosure provides a kit for analyzing a biological sample for the presence of a target nucleic acid, e.g., the nucleic acid of a pathogen. In one embodiment, the kit includes a positive internal control composition comprising an inactivated microbe according to the present disclosure. In another embodiment, the kit comprises the inactivated microbe in a liquid matrix. The liquid matrix comprises a stable biological fluid that corresponds to a fluid from which biological samples will be analyzed. Such fluids include, but are not limited to, serum, plasma, defibrinated plasma, stabilized plasma pool, cerebral spinal fluid (CSF), urine, saliva, semen, and sputum. Alternatively the liquid matrix can comprise synthetic matrices formulated to simulate such biological fluids. Methods of preparing synthetic biological fluids are well known in the art. Further, the liquid matrix can contain additives such as antioxidants, buffer salts, preservatives, antibiotics, and matrix stabilizing fillers such as sugars (monosaccharides and polysaccharides), proteins (including albumin, ovalbumin, gamma globulin, red blood cell lysates, casein, dry powdered milk, and/or other scrum proteins), and synthetic stabilizers such as poly-vinylpyrrolidine, poly-1-lysine, and methylated Bovine Serum Albumin (BSA). The liquid matrix can also be modified for lyophilization for long term storage and stability by addition of, for example, sucrose and mannose.

In the practice of the disclosure, the kit can comprise additional materials necessary for conducting nucleic acid amplification techniques known to those of ordinary skill in the art. Further, the disclosure is intended to encompass the addition of the inactivated microbes of the present disclosure to suitable kits for nucleic acid amplification techniques. In another aspect of the present disclosure, kits are provided for use in primer extension methods or nucleic acid amplification assays described herein. In some embodiments, the kit is compartmentalized for ease of use and contains at least one container providing an inactivated microbe in accordance with the present disclosure. One or more additional containers providing additional reagent(s) can also be included. In some embodiments, the kit can also include a blood collection tube, container, or unit that comprises heparin or a salt thereof, or releases heparin into solution. The blood collection unit can be a heparinized tube. Such additional containers can include any reagents or other elements recognized by the skilled artisan for use in primer extension procedures in accordance with the methods described above, including reagents for use in, e.g., nucleic acid amplification procedures (e.g., PCR, RT-PCR). For example, in certain embodiments, the kit further includes a container providing a 5' sense primer hybridizable, under primer extension conditions, to a predetermined polynucleotide template, or a primer pair comprising the 5' sense primer and a corresponding 3' antisense primer. In other, non-mutually exclusive variations, the kit includes one or more containers providing nucleoside triphosphates (conventional and/or unconventional). In specific embodiments, the kit includes alpha-phosphorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction.

While the foregoing invention has been described in some detail for purposes of clarity and understanding, it will be clear to one skilled in the art from a reading of this disclosure that various changes in form and detail can be made without departing from the true scope of the invention. For example, all the compositions and methods described above can be used in various combinations.

The following examples are given to illustrate embodiments of the present invention as it is presently preferred to practice. It will be understood that the examples are illustrative, and that the invention is not be considered as restricted except as indicated in the appended claims.

EXAMPLES

Example 1: Inactivation of Bacteriophage with Citraconic Anhydride

In order to analyze lambda bacteriophage GT11 inactivation using citraconic anhydride (also referred to as "Cit" or "cit"), a titration was performed. Table 1.1 below shows dilution of citraconic anhydride 11M.

TABLE 1.1

| Tube | Working stock | Final concentration in reaction with phage |
|---|---|---|
| 0 | 0 | 0 |
| 10-1 | 1.1M | 11 mM |
| 10-2 | 0.11M | 1.1 mM |
| 10-3 | 11 mM | 0.11 mM |
| 10-4 | 1 mM | 11 μM |
| 10-5 | 0.1 mM | 1.1 μM |

10 μl of working solution of citraconic anhydride in DMF was added to 1 ml lambda bacteriophage in SM buffer, which is 0.1 M NaCl, 10 mM $MgSO^4$, 50 mM Tris pH 7.5, 0.01% gelatin (Sambrook and Russell, supra, page A2.8) where the phage was provided at $1 \times 10^7$ pfu/ml). The reaction was performed at room temperature for 1 hour and then stored at 4° C. for 7 days to one month. The phage solutions were titered to determine the effect of the citraconic anhydride modification on the phage.

Titering of bacteriophage was performed as follows: The host bacterium, *E. coli* Y1088, was inoculated into 15 mls luria broth supplemented with 10 mM MgSO4 and 0.2% Maltose (w/v) using a 0.1% inoculum and incubated at 37° C. to an OD<=1. The cells were concentrated by centrifugation (10 minutes at 500×g) and the cell pellet resuspended in ½ volume of sterile 10 mM MgSO4. The *E. coli* cells were diluted to 0.5 OD600 with 10 mM MgSO$_4$. The bacteriophage was serially diluted in SM Buffer as follows. Pipet 10 μL phage into the tube labeled $10^{-2}$. Resuspend by vortexing. Using a new tip, pipet 10 μL of the $10^{-2}$ dilution into the tube labeled $10^{-4}$. Resuspend by vortexing. Repeat the 100-fold serial dilutions to the $10^{-8}$ tube. From the $10^{-8}$ tube, perform 10-fold dilutions to the $10^{-9}$ and $10^{-10}$ tubes. Add 100 μL of phage from the $10^{-8}$ s to the $10^{-9}$ tube, vortex, and add 100 μL from the $10^{-9}$ tube to the $10^{-10}$ tube. Vortex the $10^{-10}$ tube. Add 300 μL *E. coli* to each of 5 sterile 17×100 mm Falcon polypropylene round bottom tubes (#352057) for each sample being titered. Add 100 μL of the diluted Lambda DNA to the tube (dilutions $10^{-4}$, $10^{-6}$, $10^{-8}$, $10^{-9}$ and $10^{-10}$). Let sit 10 minutes at room temperature. Incubate 10 minutes at 37° C. Meanwhile, label the NZCYM plates with the phage sample and the dilution. To the first tube still in the 37° C. heat block, add 3 mL top agar (from the bottle of top agar in the 50° C. bath), vortex the tube, and quickly pour onto the NZCYM plate. Swirl the plate quickly so the top agar covers the entire plate. Allow the top agar to solidify on the bench. Repeat with each tube. Incubate the plates at 37° C. overnight in an inverted position. The next day, count the plaques and calculate the titer by using the dilution which provides the most countable number of plaques.

Table 1.2 below provides the results for day 1 and day 8, 11 mM was found to provide complete inactivation, which persisted after 7 days.

TABLE 1.2

| Final concentration in reaction with phage | Day 1 - Titer (pfu/ml) | Day 8 - Titer (pfu/ml) |
| --- | --- | --- |
| 0 | $9.1 \times 10^6$ | $2.8 \times 10^7$ |
| 11 mM | 0 | 0 |
| 1.1 mM | $1.8 \times 10^6$ | $2.0 \times 10^7$ |
| 0.11 mM | $5.5 \times 10^6$ | $3.6 \times 10^7$ |
| 11 μM | $9.0 \times 10^6$ | $2.9 \times 10^7$ |
| 1.1 μM | $6.7 \times 10^6$ | $3.9 \times 10^7$ |

Example 2: Amplification from Citraconic Anhydride-Inactivated Bacteriophage

This experiment tested the effect of citraconic anhydride (Cit) treatment of lambda bacteriophage on DNA amplification. The treatment was done at 3 different concentrations, before being titrated and titered. Table 2.1 below provides the treatment conditions used in the experiment (0A-0C: control DMF only; 1A-1C: highest Cit concentration; 2A-2C: middle Cit concentration; and 3A-3C: lowest Cit concentration).

TABLE 2.1

| Sample | Concentration of Cit | Concentration of phage |
| --- | --- | --- |
| 0A | 0 | $1 \times 10^4$ copies/uL |
| 0B | 0 | $1 \times 10^3$ copies/uL |

TABLE 2.1-continued

| Sample | Concentration of Cit | Concentration of phage |
| --- | --- | --- |
| 0C | 0 | $1 \times 10^2$ copies/uL |
| 1A | 11 mM | $1 \times 10^4$ copies/uL |
| 1B | 11 mM | $1 \times 10^3$ copies/uL |
| 1C | 11 mM | $1 \times 10^2$ copies/uL |
| 2A | 1.1 mM | $1 \times 10^4$ copies/uL |
| 2B | 1.1 mM | $1 \times 10^3$ copies/uL |
| 2C | 1.1 mM | $1 \times 10^2$ copies/uL |
| 3A | 0.11 mM | $1 \times 10^4$ copies/uL |
| 3B | 0.11 mM | $1 \times 10^3$ copies/uL |
| 3C | 0.11 mM | $1 \times 10^2$ copies/uL |

Twenty microliters of diluted phage was added to 400 microliters of diluted whole blood and the nucleic acids were purified using the Magnapure compact (Roche) and the MagNA Pure Compact Nucleic Acid Isolation Kit I—Large Volume (Cat no. 03 730 972 001). The 100 μl eluate was stored at 4° C. till amplified. Five microliters of sample was combined with 15 μl LCVM mastermix containing primers and amplified on the LC480 themocycler (Roche). Profile: 95° C. 30 seconds, followed by 55 cycles of 95° C. 5 seconds, 60° C. 30 seconds.

FIG. 1 provides the results of the experiment. As shown in Table 2.2 below, phage treated with 11 mM Cit had the same Ct as untreated (active) phage.

TABLE 2.2

| Concentration of Cit | Copies/reaction | Average Cp |
| --- | --- | --- |
| 0 mM | 5000 | 25.28 |
| 11 mM | 5000 | 25.30 |
| 1.1 mM | 5000 | 25.25 |
| 0.11 mM | 5000 | 25.18 |
| 0 mM | 500 | 28.73 |
| 11 mM | 500 | 27.89 |
| 1.1 mM | 500 | 28.71 |
| 0.11 mM | 500 | 28.82 |
| 0 mM | 50 | 32.35 |
| 11 mM | 50 | 31.19 |
| 1.1 mM | 50 | 32.24 |
| 0.11 mM | 50 | 32.36 |

Example 3: Stability of Citraconic Anhydride-Inactivated Bacteriophage

This experiment tested the stability of citraconic anhydride (Cit)-treated lambda bacteriophage. Phage was inactivated using different Cit concentrations and stored for one month at 4° C. As shown in Table 3.1, phage inactivated at greater than or equal to 11 mM was found to remain inactivated for 1 month.

TABLE 3.1

| Working stock | Final Cit concentration in reaction with phage | Titer pfu/ml (Day 1) | Titer pfu/ml (at 1 month) |
| --- | --- | --- | --- |
| 0 | 0 | $6.5 \times 10^6$ | $1.4 \times 10^6$ |
| 2.2M | 22 mM | 0 | 0 |
| 1.1M | 11 mM | 0 | 0 |
| 0.55 mM | 5.5 mM | $1.5 \times 10^6$ | $1.5 \times 10^6$ |

Example 4: DNase Sensitivity

This experiment tested the DNase sensitivity of citraconic anhydride (Cit)-treated lambda bacteriophage. Different targets were tested using either 0.5 units or 0.05 units of DNase (RPC diluent+0.095% NaAzide). Forty microliters of phage were combined with 4 μl 10× Reaction buffer (400 mM Tris-HCl, pH 7.9, 100 mM NaCl, 60 mM MgCl2, 10 mM CaCl2) and 1 μl diluted DNaseI, incubated at 37° C. for 20 minutes. The reaction was terminated by adding 2 uL of 0.2M EDTA. Following DNase treatment, the phage were added to whole blood samples and treated as outlined above using the MagNA Pure Compact.

Table 4.1 provides information on the targets tested using 0.5 units of DNase. Table 4.2 provides information on the targets tested using 0.05 units of DNase.

TABLE 4.1

| DNase target tested | Concentration | Cit Treatment |
|---|---|---|
| Naked plasmid (no phage) | $1 \times 10^7$ copies/mL | None |
| Phage in 0.095% NaAzide Buffer | $1 \times 10^6$ copies/mL | None |
| Phage in DMF Buffer | $1 \times 10^7$ copies/mL | None |
| Phage - 5.5 mM Cit | $1 \times 10^7$ copies/mL | 0.5M |
| Phage - 11 mM Cit | $1 \times 10^7$ copies/mL | 1.0M |
| Phage - 22 mM Cit | $1 \times 10^7$ copies/mL | 2.0M |

TABLE 4.2

| DNase target tested | Concentration | |
|---|---|---|
| Naked plasmid (no phage) | $1 \times 10^6$ copies/mL | |
| Phage in 0.095% NaAzide Buffer | $1 \times 10^6$ copies/mL | |
| Phage in DMF Buffer | $3.33 \times 10^5$ copies/mL | No Cit treatment |
| Phage - 5.5 mM Cit | $3.33 \times 10^5$ copies/mL | 0.5M Cit treatment |
| Phage - 11 mM Cit | $3.33 \times 10^5$ copies/mL | 1.0M Cit treatment |
| Phage - 22 mM Cit | $3.33 \times 10^5$ copies/mL | 2.0M Cit treatment |

Forty microliters of phage were combined with 4 μl 10× Reaction buffer (400 mM Tris-HCl, pH 7.9, 100 mM NaCl, 60 mM MgCl2, 10 mM CaCl2)) and 1 μl diluted DNaseI, incubated at 37° C. for 20 minutes. The reaction was terminated by adding 2 uL of 0.2M EDTA. Following DNase treatment, the phage were added to whole blood samples and treated as outlined above using the MagNA Pure Compact.

Samples were treated with 0.5 units or 0.05 units of DNase per reaction. No heat inactivation of the DNase was performed and the samples were added to diluted blood. Sample preparation was performed immediately on the MagNA Pure Compact Instrument to remove all DNase. Amplification and detection was performed via qPCR (see protocol provided in Example 2). A control with no DNase treatment was also exposed to reaction buffer at 37° C. and also subjected to sample preparation.

Figure 2:
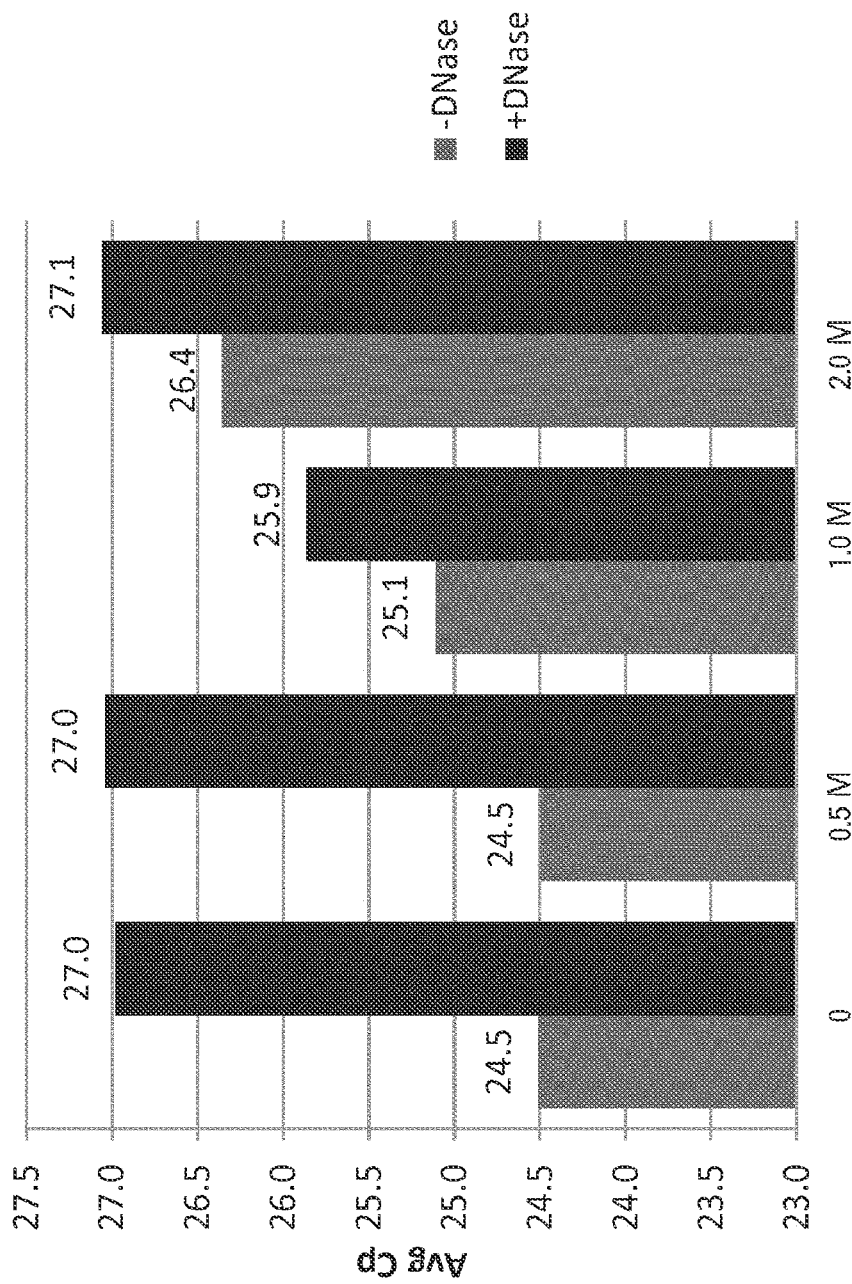
FIG. 2 shows the results of nucleic acid amplification from citraconic anhydride-inactivated bacteriophage following DNase treatment.
Figure 3:
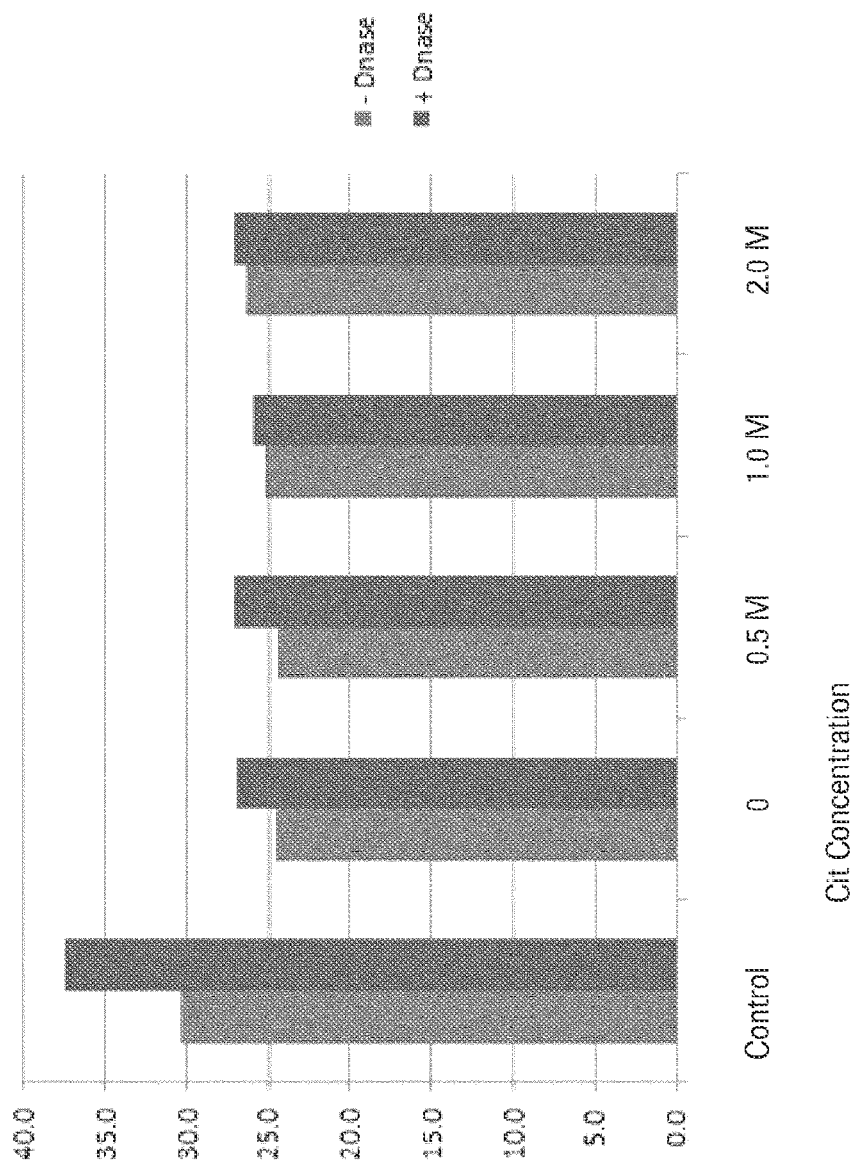
FIG. 3 shows the results of nucleic acid amplification from citraconic anhydride-inactivated bacteriophage following DNase treatment.

FIG. 2 provides the results of DNase treatment at 0.5 units. FIG. 3 provides the results of DNase treatment at 0.05 units. Table 4.3 provides the change in Cp (Δ Cp) between treated and untreated targets. Phage was initially treated at a concentration of $1 \times 10^7$ copies/mL and then diluted 30-fold in RPC diluent+0.95% NaAzide so that the Cp would be similar to the lower concentration of the control phage at ~29 cycles.

TABLE 4.3

| | ±0.5 Units DNase | | | ±0.05 Units DNase | | |
|---|---|---|---|---|---|---|
| Target | −DNase | +DNase | Δ Cp | −DNase | +DNase | Δ Cp |
| Plasmid | 30.4 | 37.5 | 7.1 | 30.0 | 35.0 | 5.0 |
| Phage | 28.9 | 34.4 | 5.4 | 29.0 | 32.3 | 3.3 |

TABLE 4.3-continued

| | ±0.5 Units DNase | | | ±0.05 Units DNase | | |
|---|---|---|---|---|---|---|
| Target | −DNase | +DNase | Δ Cp | −DNase | +DNase | Δ Cp |
| 60A | 28.7 | 35.6 | 6.9 | 28.6 | 32.3 | 3.7 |
| 70A | 28.7 | 36.8 | 8.0 | 28.6 | 32.2 | 3.6 |
| No Cit | 24.5 | 27.0 | 2.5 | 29.5 | 32.3 | 2.8 |
| 0.5M Cit | 24.5 | 27.0 | 2.5 | 29.5 | 32.2 | 2.7 |
| 1.0M Cit | 25.1 | 25.9 | 0.8 | 30.8 | 35.1 | 4.3 |
| 2.0M Cit | 26.4 | 27.1 | 0.7 | 31.8 | 34.0 | 2.2 |

Targets treated with 0.05 units of DNase were also re-tested after storage for 1 week and 1 month. If any additional DNase activity against target occurs, the enzyme was expected to remove any unprotected target and a Cp shift would occur when amplified by qPCR. Parallel experiments were performed where the targets was stored in SM Buffer (as per Example 1).

Figure 4:
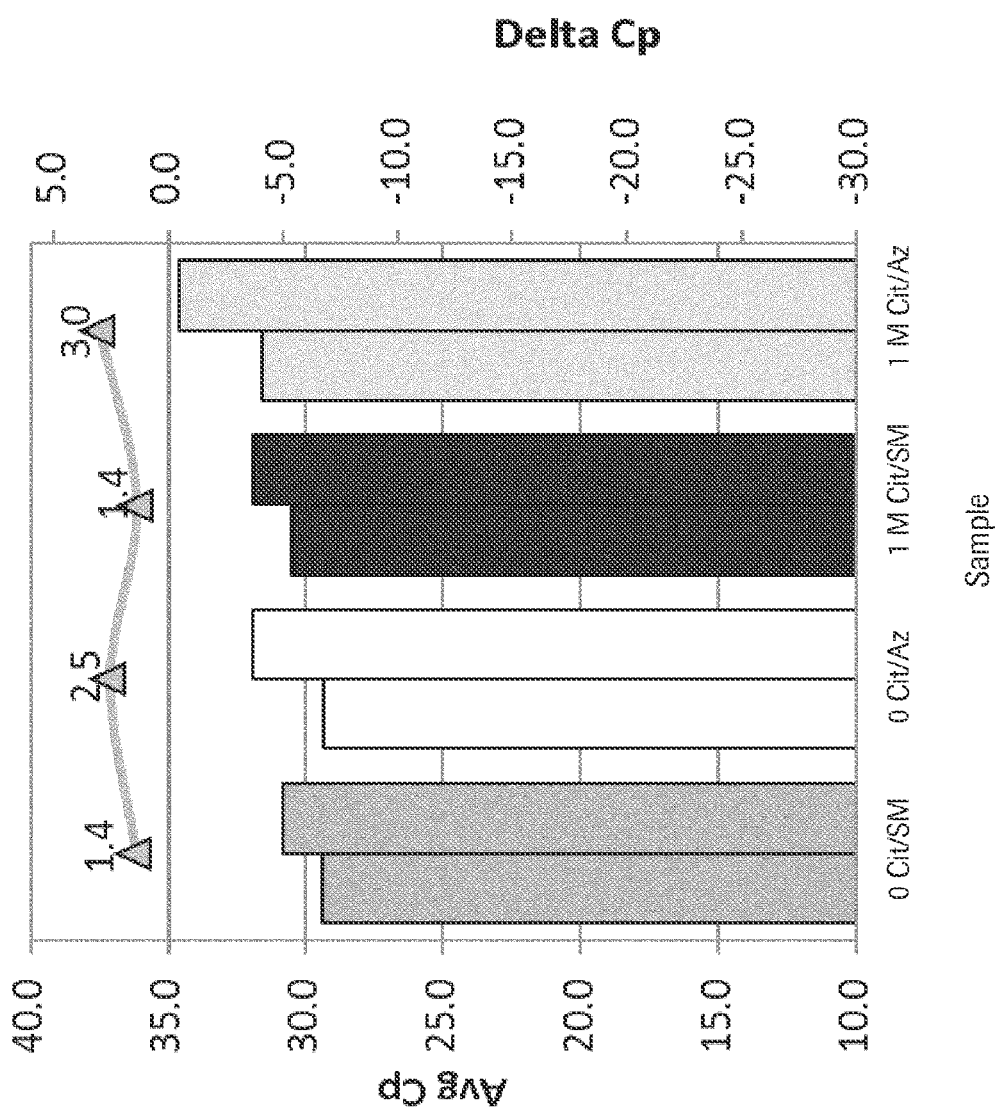
FIG. 4 shows the results of nucleic acid amplification from citraconic anhydride-inactivated bacteriophage following DNase treatment and 1 week of storage.

FIG. 4 shows the results of DNA amplification (according to protocol in Example 2) following DNase treatment and 1 week of storage in either RPC Diluent+0.095% NaAzide or SM Buffer (as per Example 1). The change (Δ) in Cp is shown across the top of the graph and summarized below in Table 4.4. The left bar is −DNase and the right bar is +DNase.

TABLE 4.4

| Sample | Avg. Cp: No DNase treatment | Avg. Cp: DNase treatment | Δ in Cp after 1 week |
|---|---|---|---|
| No Cit treatment in SM buffer | 29.4 | 30.8 | 1.4 |
| No Cit treatment in NaAzide buffer | 29.4 | 31.9 | 2.5 |
| 1M Cit treatment in SM buffer | 30.5 | 31.9 | 1.4 |
| 1M Cit treatment in NaAzide buffer | 31.6 | 34.6 | 3.0 |

Figure 5:
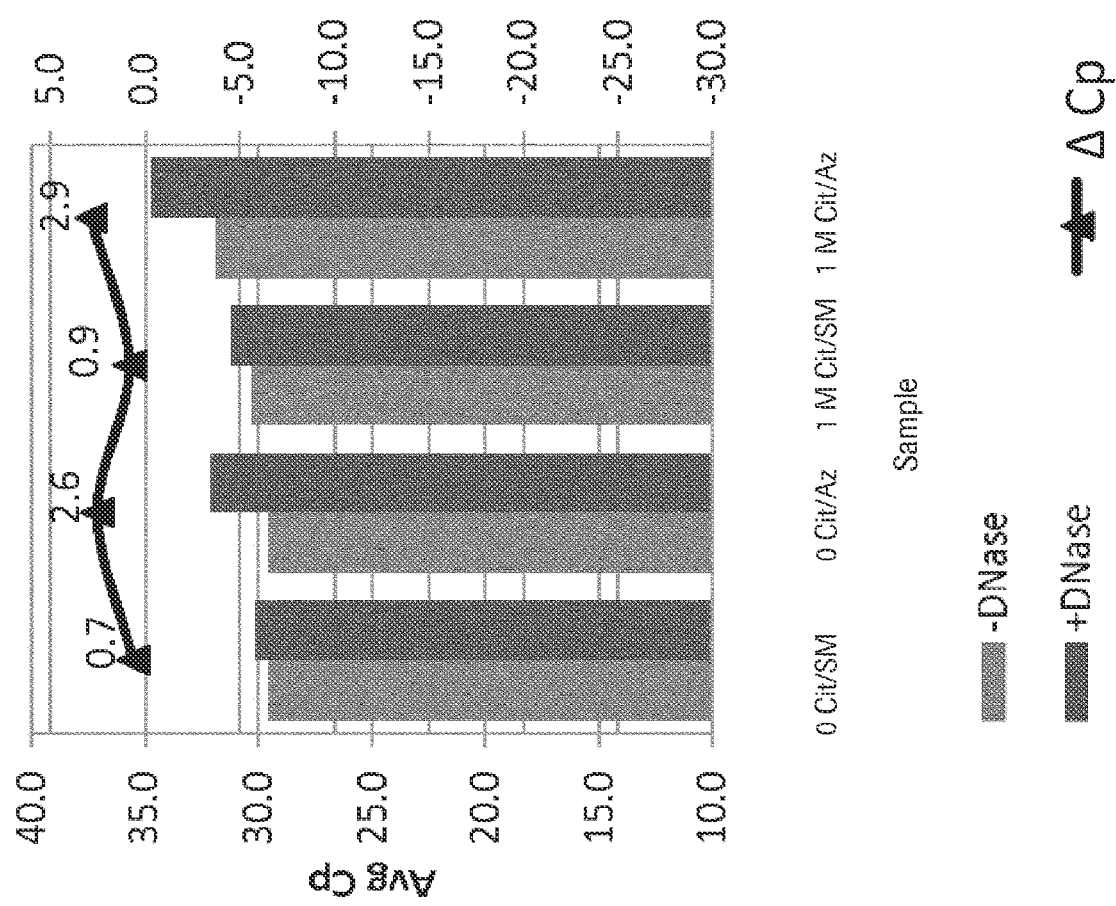
FIG. 5 shows the results of nucleic acid amplification from citraconic anhydride-inactivated bacteriophage following DNase treatment and 1 month of storage.

FIG. 5 shows the results of DNA amplification (according to protocol in Example 2) following DNase treatment and 1 month of storage in either RPC Diluent+0.095% NaAzide or SM Buffer (as per Example 1). The change (Δ) in Cp is shown across the top of the graph and summarized below in Table 4.5.

TABLE 4.5

| Sample | Avg. Cp: No DNase treatment | Avg. Cp: DNase treatment | Δ in Cp after 1 week |
|---|---|---|---|
| No Cit treatment in SM buffer | 29.5 | 30.2 | 0.7 |
| No Cit treatment in NaAzide buffer | 29.6 | 32.1 | 2.6 |
| 1M Cit treatment in SM buffer | 30.3 | 31.2 | 0.9 |
| 1M Cit treatment in NaAzide buffer | 31.9 | 34.7 | 2.9 |

Example 5: Storage of Inactivation Targets

Bacteriophage targets treated with different concentrations of Cit were stored in different buffers and then evaluated for their inactivation status. Targets were stored in either 10 mM Tris pH8.3 or 10 mM Tricine pH 8.3. Table 5.1 summarizes the results, which demonstrate that Cit-treatment at >=11 mM provides inactivation for 1 month after storage in either buffer.

TABLE 5.1

| Cit Sample | Tris | | Tricine | |
|---|---|---|---|---|
| | Day 1 | After 1 month | Day 1 | After 1 month |
| 22 mM | 0 | 0 | 0 | 0 |
| 11 mM | 0 | 0 | 0 | 0 |
| 5.5 mM | $1.5 \times 10^3$ pfu/ml | 0 | $1 \times 10^3$ pfu/ml | $3 \times 10^3$ pfu/ml |
| 0 mM | $2 \times 10^5$ pfu/ml | $1.5 \times 10^4$ pfu/ml | $6.8 \times 10^9$ pfu/ml | $7.7 \times 10^4$ pfu/ml |

The invention claimed is:

1. A method of verifying a detection result for a test sample in a nucleic acid amplification assay, the method comprising
(a) performing sample preparation on a mixture comprising a test sample and an inactivated microbe, comprising preparing a sample preparation mixture comprising exogenous inactivation of an infectious microbe, wherein the infectious microbe is in a formulation of an internal control reagent, the method comprising: (i) exogenously contacting the infectious microbe containing an internal control nucleic acid with an effective amount of citraconic anhydride, thereby inactivating the microbe while preserving the integrity of the internal control nucleic acid sequence, and (ii) contacting the infectious microbe with a sample preparation reagent, and wherein prior to contacting the infectious microbe with the effective amount of citraconic anhydride, the infectious microbe comprises a proteinaceous outer surface comprising at least one primary amine group, wherein the infectious microbe is a bacteriophage, wherein the internal control reagent is a full process internal control reagent, and wherein the sample preparation reagent is selected from the group consisting of a protease, a solid support material, and a lysis buffer, wherein the sample preparation releases nucleic acid from both the test sample and the inactivated microbe;
(b) performing nucleic acid amplification on the released nucleic acid; and
(c) detecting the control nucleic acid target, thereby verifying the detection result.

2. The method of claim 1, wherein the inactivated microbe comprises a proteinaceous outer surface comprising at least one primary amine group modified to an amide linkage and a terminal carboxylate.

3. The method of claim 1 or 2, wherein the effective amount of citraconic anhydride is at a concentration between about 5 mM and about 25 mM.

4. The method of claim 3, wherein the effective amount of citraconic anhydride is at a concentration selected from the group consisting of about 5.5 mM, about 1 mM, and about 2 mM.

5. The method of claim 1, wherein the step of exogenously contacting the infectious microbe containing an internal control nucleic acid sequence with an effective amount of citraconic anhydride is performed at ambient temperature and/or is performed for about 1 hour.

* * * * *